United States Patent [19]

Marrelli et al.

[11] Patent Number: 5,107,219

[45] Date of Patent: Apr. 21, 1992

[54] MEANS AND METHOD FOR DETERMINING THE CONDUCTANCE OF A FLUID

[75] Inventors: John D. Marrelli, Houston; Lisa L. Pepin, Sugar Land; Gregory J. Hatton, Houston; Farhan Siddiqui, Katy; Joseph D. Stafford, Bellaire, all of Tex.

[73] Assignee: Texaco Inc., White Plains, N.Y.

[21] Appl. No.: 637,023

[22] Filed: Jan. 3, 1991

[51] Int. Cl.[5] .................... G01N 22/00; G01R 27/04
[52] U.S. Cl. .................................. 324/640; 324/698; 324/643
[58] Field of Search ............. 324/640, 643, 694, 698; 73/61.1 R, 73; 374/122, 142

[56] References Cited

U.S. PATENT DOCUMENTS

| | | | |
|---|---|---|---|
| 4,902,961 | 2/1990 | De | 324/640 |
| 4,947,127 | 8/1990 | Helms | 324/640 |
| 4,947,128 | 8/1990 | Hatton | 324/640 |
| 4,947,129 | 8/1990 | Helms | 324/640 |
| 4,977,377 | 12/1990 | Durrett | 324/640 |
| 5,001,434 | 3/1991 | Marrelli | 324/640 |
| 5,014,010 | 5/1991 | Helms | 324/640 |

*Primary Examiner*—Kenneth A. Wieder
*Assistant Examiner*—Jose M. Solis
*Attorney, Agent, or Firm*—Robert A. Kulason; James J. O'Loughlin; Ronald G. Gillespie

[57] ABSTRACT

The conductance meter includes source means which irradiates a fluid with microwave energy. A receiver receives microwave energy that has passed through the fluid and provides the received microwave energy as test microwave energy. Electronic apparatus determines the conductance of the fluid in accordance with the amplitude of the test microwave energy and the phase difference between the microwave energy from the source and the test microwave energy from the receiver where only 1 microwave frequency is used.

4 Claims, 3 Drawing Sheets

MEANS AND METHOD FOR DETERMINING THE CONDUCTANCE OF A FLUID

BACKGROUND OF THE INVENTION

1. Field of the Invention

The present invention relates to apparatus and methods for determining the conductance of a fluid in general and more particularly, to a fluid that has at least two different components such as water and oil.

2. Summary of the Invention

The conductance meter includes source means which irradiates a fluid with microwave energy. A receiver receives microwave energy that has passed through the fluid and provides the received microwave energy as test microwave energy. Electronic apparatus determines the conductance of the fluid in accordance with the amplitude of the test microwave energy and the phase difference between the microwave energy from the source and the test microwave energy from the receiver.

DESCRIPTION OF THE INVENTION

Figure 1:
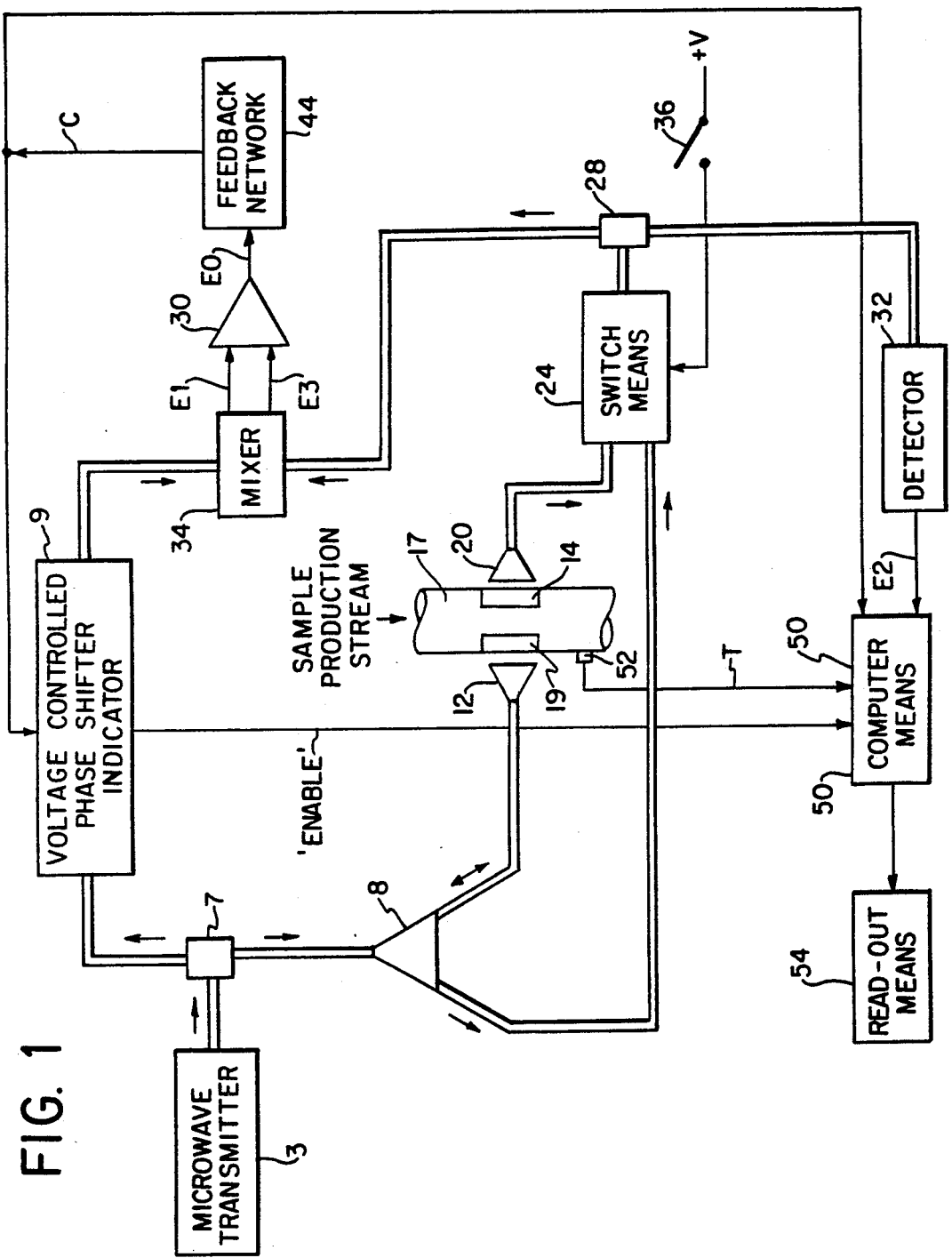
FIG. 1 is a conductance meter, constructed in accordance with the present invention, shown in partially schematic form and in partially simplified block diagram form.

The analyzer shown in FIG. 1 includes a microwave source 3 providing an electromagnetic energy, hereinafter referred to as microwave energy. Source 3 is low powered and may use a microwave gun source. Source 3 provides the microwave energy to a directional coupler 7. Directional coupler 7 provides the selected microwave energy to a circulator 8 and to a conventional type voltage controlled phase shifter 9. All conductance or carrying of microwave energy is accomplished by using conventional type waveguides.

Circulator 8 provides microwave energy to an antenna 12. Antenna 12 provides the microwave energy through a window 14, which may be made of a conductive ceramic or Teflon, to a petroleum stream having at least oil and water, passing through a pipe 17. Pipe 17 may be a portion of a pipeline having windows 14 or it may be made of the "window" material. The microwave energy provided by antenna 12 passes through the petroleum stream and another window 14 and is received by an antenna 20. Antenna 20 provides the received microwave energy to a switch means 24 which in turn provides the received microwave as test microwave energy to a directional coupler 28, as hereinafter explained. Directional coupler 28 provides the test microwave energy to a detector 32 and to a mixer 34. Detector 32 provides a signal E2 corresponding to the intensity of the microwave energy received by antenna 20.

The petroleum stream also reflects some of the microwave energy back to antenna 12 which passes back through antenna 12 to circulator 8. Circulator 8 blocks the reflected microwave energy from feeding back to source 3 and provides the reflected microwave energy to switch means 24. Reflected microwave energy becomes more important as the distance between antennas 12 and 20 increases. This is especially true where a large pipeline carrying the petroleum stream is being monitored.

A positive direct current voltage +V is provided to a switch 36 which is connected to switch means 24. With switch 36 open, switch means 24 provides microwave energy from antenna 20 as the test microwave energy. When switch 36 is closed, the reflected microwave energy from circulator 8 is provided by switch means 24 as the test microwave energy.

The microwave energy from voltage controlled phase shifter 9, hereinafter called the reference microwave energy, and the test microwave energy from directional coupler 28, are provided to mixer 34 which mixes them to provide two electrical signals E3, E4, representative of the phases of the reference microwave energy and the test microwave energy, respectively.

A differential amplifier 30 provides an output signal EO in accordance with the difference between signals E3 and E4. Signal EO is a function of the phase difference between the reference microwave energy and the test microwave energy and is provided to a feedback network 44. Feedback network 44 provides a signal C to voltage control phase shifter 5, controlling the phase of the reference microwave energy, and to a mini-computer means 50. Signal Eo, and hence the signal C, decreases in amplitude until there is substantially 90° phase difference between the reference microwave energy and the test microwave energy. Voltage control phase shifter 5 indicates the amount of phase shift required to eliminate the phase difference.

Signal E2 from detector 32 is also provided to computer means 50. It has been discovered that the phase difference for measurements in a fluid stream may exceed 360 degrees under certain circumstances. These circumstances include cases where the dielectric of the stream is large, for example when the percentage of water in the petroleum is large, and when the emulsion is water continuous and in cases where the distance between antennas is large as in the case of using larger pipe 17 of FIG. 1. The most accurate functioning of the oil-in-water conductance meter requires that the emulsion be water continuous for at least one sample or approximately several milliseconds during either a flowing or no-flow case. In normal operation many emulsions show short time periods in which the fluid or a small portion of it is in a water continuous state. In cases where no naturally occurring water continuous states are found, injection of a surface active agent can be used which is designed to break oil continuous emulsions into water continuous emulsions. There are cases when less accuracy can be tolerated and in which oil continuous emulsions are always present.

In many of those cases the true phase shift may be the measured phase shift plus some integer multiple of 360 degrees. The present invention resolves this ambiguity by monitoring the attenuation of the microwave energy, and using the amplitude of attenuation or an index to determine the correct integer multiplier to use when computing the true phase shift. The correct integer is chosen from a table created from knowledge of the frequency involved. The maximum possible size of the integer that may be resolved is limited by the attenuation range. In the present case integer size of up to 3 can be resolved.

A temperature sensor 52 sensing the temperature of the petroleum stream in pipe 17 and provides a signal T to computer means 50 representative of the sensed temperature.

Phase shifter 9 also provides an enable signal to computer means 50 allowing computer means 50 to utilize signals T, C and E2. Computer means 50 also provides signal E1 to switch means 4 so that computer means 50 can correlate signal E2 to a particular frequency.

Figure 2:
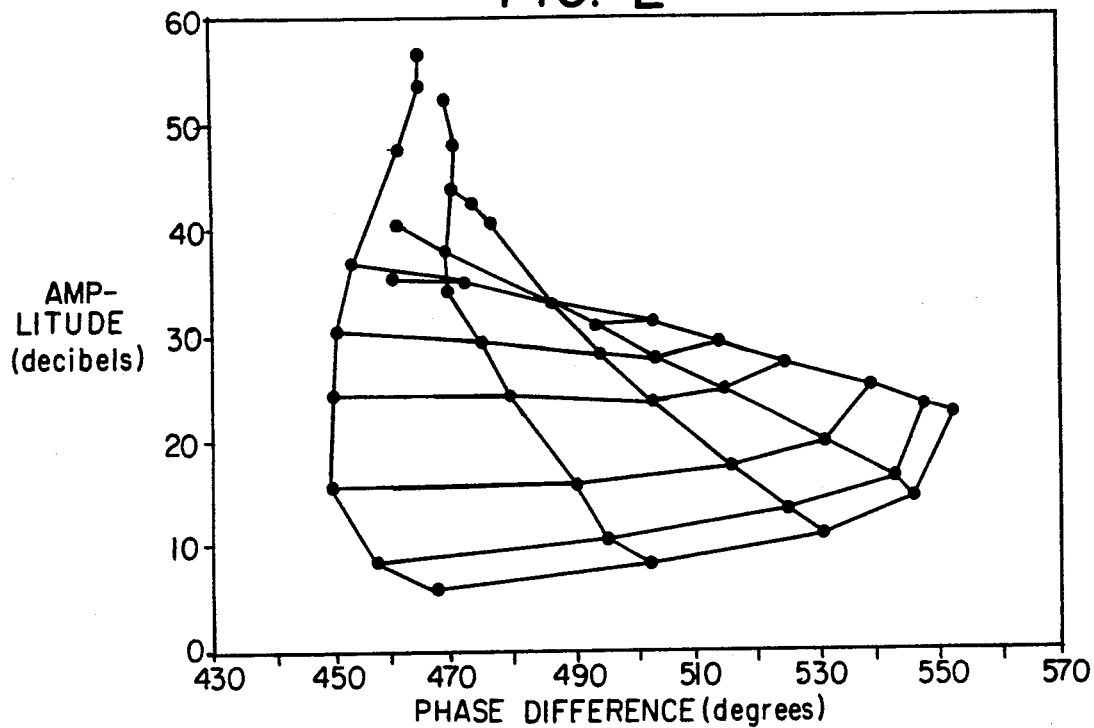
FIG. 2 is a map of phase shift versus attenuation for large numbers of known mixtures of solutions over a wide range of temperature.
Figure 3:
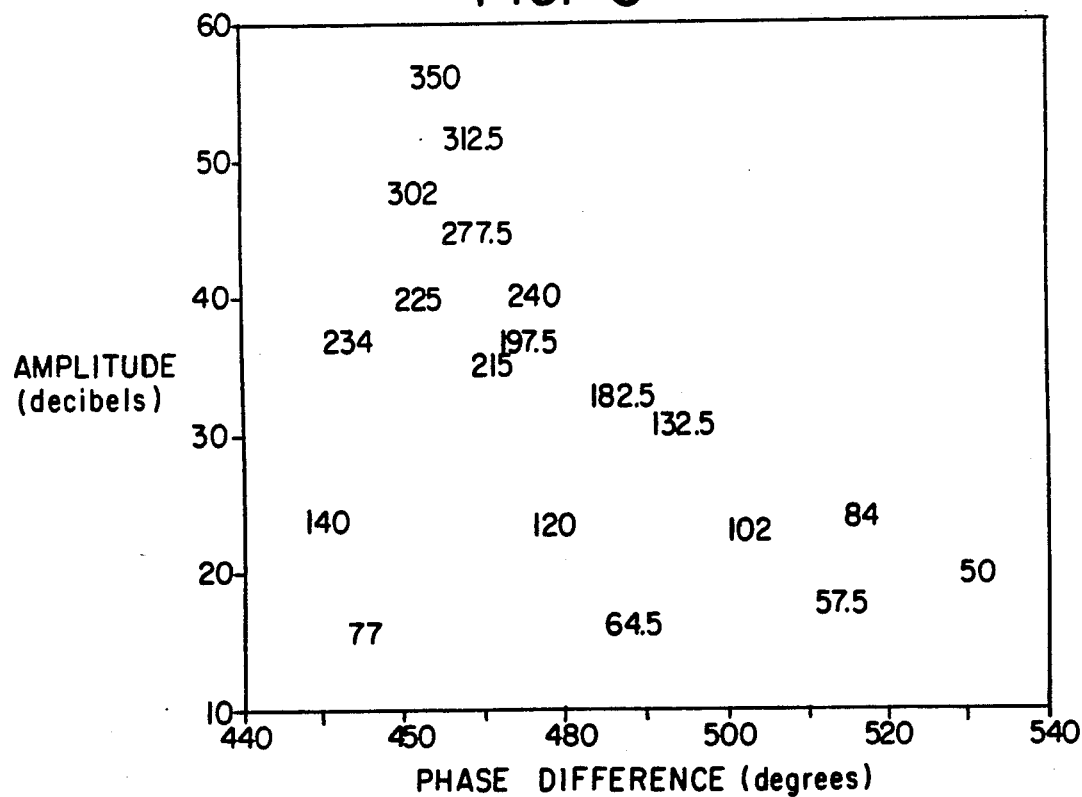
FIG. 3 is a graphical representation of conductance lines plotted against amplitude versus phase difference.
Figure 4:
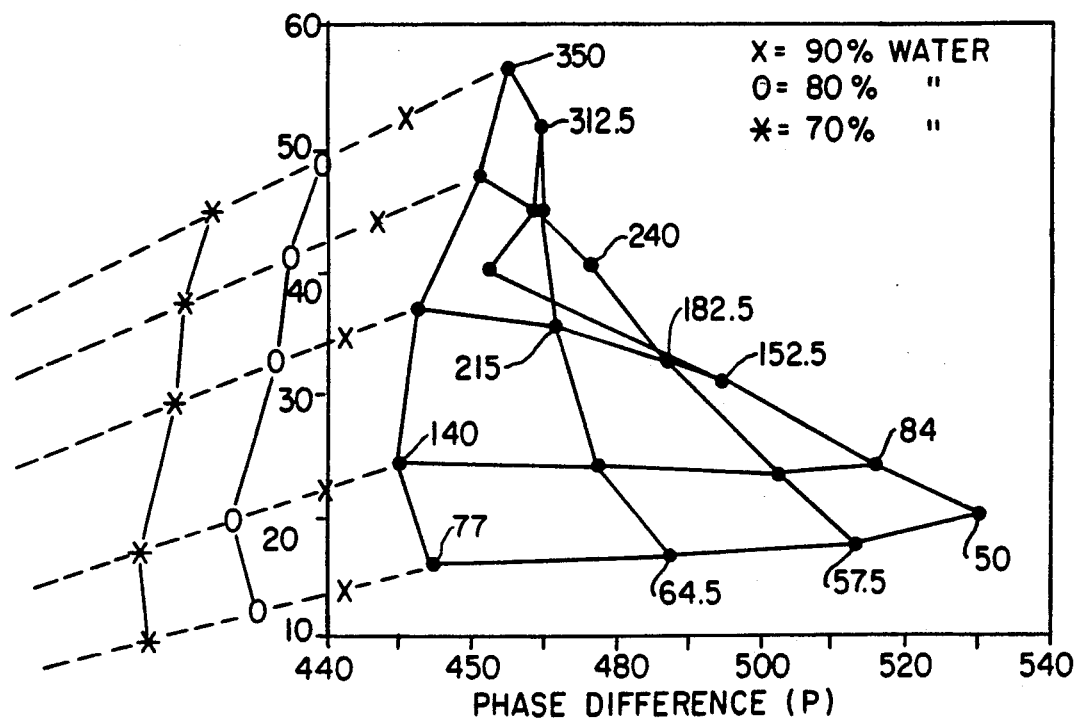
FIG. 4 is a graphical representation with detailed and dashed lines showing detailed information at temperature 75° for example of turbulent mixing of aqueous solutions used in FIGS. 2 and 3.

Computer means 50 has stored within it tables related to a microwave energy phase shift and attenuation map for large numbers of known mixtures of solutions over a wide range of temperatures (0° to 100° C). One such map is shown in FIG. 2, another such map is shown in FIG. 4. The conductivity of the solutions used may also be mapped onto the same graph as shown in FIG. 3 and FIG. 4. In FIG. 4, the effect of continuous turbulent mixing of the aqueous solutions used in FIGS. 2 and 3 are shown with oil, in this case dodecane paraffin oil.

Each dotted line in FIG. 4 represents successively higher ratios of dodecane paraffin oil-to-water of the indicated salinity and conductivity as the dotted line is followed to the left and down. Because the line defining the various water continuous mixtures is a straight line, it has been found that the slope of the line is a constant for any chosen water conductivity. Furthermore, changing the type of oil used does not change the slope of the line to a significant degree.

These figures demonstrate the principle of operation of the oil-in-water conductance meter as follows. Measurement of the amplitude (Al) and phase shift (Pl) of any water continuous mixture of oil and water will give a constant ratio M in the following equation (1)

$$M = (A1 - AO)/(P1 - PO), \quad (1)$$

where AO and PO are the amplitude and phase difference measurements of the oil mixed with the water for one test or where AO=10 and PO=0. It has been discovered that M is approximately constant for any combination of oil and a given salt water at a given temperature and when the water is the continuous phase.

Figure 5:
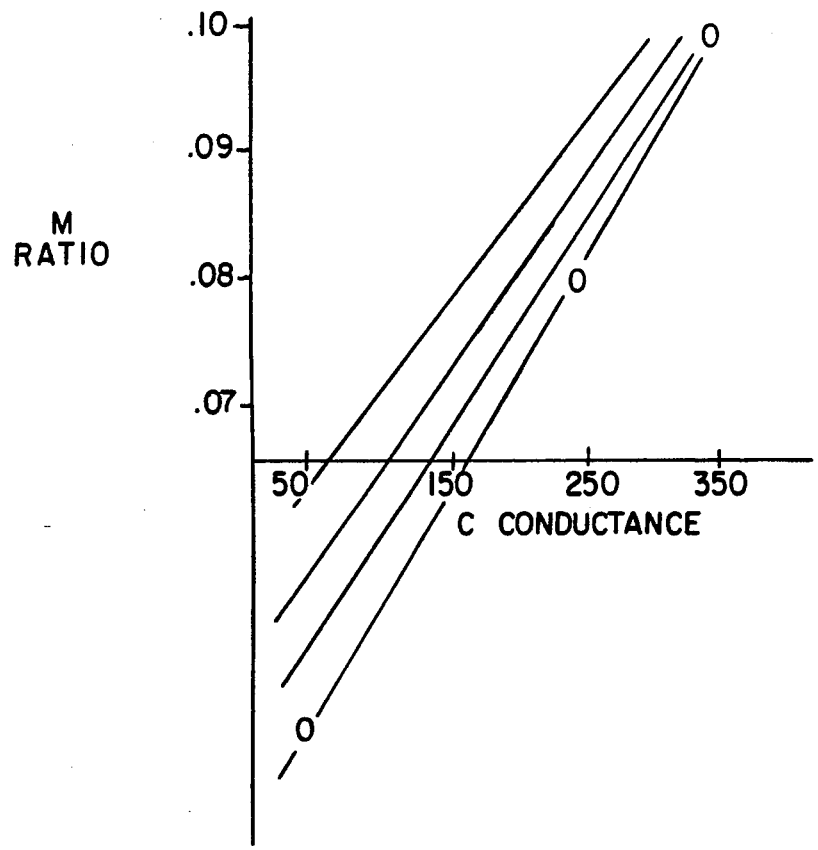
FIG. 5 represents the plot of slope k of the dotted lines of FIG. 4 versus the conductivity of water at each temperature used.

FIG. 5 presents the plot of the constant ratio M versus the conductivity of the water at each temperature used. This plot demonstrates a clear relationship between M and conductivity C and temperature. This relationship is shown in equation (2) where:

$$C = k*M + 1 \quad (2)$$

where c is conductivity, M is the ratio defined in equation 1, k is the slope of the relationship in FIG. 5 and 1 is the intercept of the regression line fitting the data of FIG. 5. Both k and l may be further modeled by regression analysis to allow c to be written in simple closed form in the following equation (3):

$$C = f(M, T) \quad (3)$$

where T is temperature. Further rewriting of equation 3 leads to:

$$fC = (A, P, T) \quad (4)$$

indicating that the oil-in-water conductance meter measurements of amplitude A, phase shift P and temperature T of the solution, can be directly converted to conductivity regardless of the presence of contaminating oils in the water sample.

While equation (4) is shown here to be graphically developed from relationships easily modeled by straight lines it is not limited to linear relationships.

In the case of oil continuous mixtures, the principle of the oil/water mixture operation is as follows.

Data point P, of FIG. 4 is determined from oil continuous mixtures by methods described in U.S. Pat. Nos. 4,947,128 and 4,947,127. The map of FIG. 4 indicates predetermined values of amplitude and phase shift due to test mixtures of oil and water of various conductables at the appropriate temperature. The salinity of the water in the test case is determined from a look-up table containing coefficients of equations which describe the curves in FIG. 4. Data Point P is tested to determine if it falls on any of the solid lines which were based on empirical lab data. If P falls on a line the conductivity of the water used to create that line is reported as the conductivity. If P does not fall on the line conductivity is reported based on a lines interpretation between empirically determined lines. Accuracy is thus determined by the number of laboratory determined water/oil mixtures at different conductivities.

What is claimed is:

1. A conductance meter comprising:
    irradiation means for irradiating a fluid with microwave energy,
    temperature sensing means for sensing the temperature of the fluid and providing a temperature signal corresponding thereto,
    receiving means for receiving microwave energy that has passed through the fluid and providing the received microwave energy as test microwave energy,
    deriving means connected to the irradiation means, to the receiving means and to the temperature sensing means for deriving the conductance of the fluid in accordance with the temperature signal, an amplitude of the test microwave energy and a phase difference between the microwave energy from the irradiation means and the test microwave energy from the receiving means; and
    in which the deriving means includes:
        means for determining a constant ratio $M_T$ at a sensed temperature, of any water continuous mixture of oil/water in accordance with the following equation:

$$M_T = (A1 - AO)/(P1 - PO),$$

where AO and PO are first amplitude and phase difference measurements of the fluid or where A1 and P1 are second amplitude and phase difference measurements of the fluid.

2. A conductance meter as described in claim 1 in which the conductivity of the fluid is determined in accordance with the following equation:

$$C = K*M + 1,$$

where C is a conductivity, M is the constant ratio and k is the slope of the relationship of the M ratio versus the conductivity C.

3. A meter as described in claim 1 in which the deriving means includes:

memory means having stored in their data relating to conductivity amplitude, phase measurement and temperature for selecting the proper conductance value in accordance with the amplitude and phase signals and temperature signals.

4. A conductance meter as described in claim 3 in which the conductivity of the fluid is determined in accordance with the following equation:

$$C = K*M + 1,$$

where C is a conductivity, M is the constant ratio and k is the slope of the relationship of the M ratio versus the conductivity C.

* * * * *